United States Patent [19]

Nevalainen

[11] 4,105,971
[45] Aug. 8, 1978

[54] PERMEABILITY RESPONSIVE OSCILLATOR FOR DETECTING PHASE TRANSFORMATIONS AT VARIOUS COOLING RATES

[76] Inventor: Harri Nevalainen, Terästehdas B 99, 55100 Imatra 1, Finland, 55100

[21] Appl. No.: 722,475

[22] Filed: Sep. 13, 1976

[30] Foreign Application Priority Data

Sep. 11, 1975 [FI] Finland .................................. 752545

[51] Int. Cl.² ............................................. G01R 33/12
[52] U.S. Cl. ..................................... 324/203; 324/224; 324/227; 324/236
[58] Field of Search ......................... 324/34 R, 34 TE; 250/341; 73/16

[56] References Cited

U.S. PATENT DOCUMENTS 3,239,826  3/1966  Yetter .................................. 340/195
3,377,838  4/1968  Kanazawa et al. ...................... 73/16

FOREIGN PATENT DOCUMENTS 2,304,693  8/1973  Fed. Rep. of Germany ........... 250/341
1,385,198  2/1975  United Kingdom ................. 324/34 TE

OTHER PUBLICATIONS

Perekos et al., An Automatic Unit for Determining the Curie Temperature of Ferromagnetic Material; Zavodskaya Lab. (USSR), vol. 41, No. 1, pp. 61-62; Jan. 1975.

*Primary Examiner*—Robert J. Corcoran
*Attorney, Agent, or Firm*—Wigman & Cohen

[57] ABSTRACT

A device for detecting phase transformations in a magnet material is disclosed. A sample is placed in a coil coupled to a harmonic oscillator and subjected to heat radiation means for simulating predetermined heating and cooling rates which result in phase transformations within the material being tested. The phase transformations are a function of changes in magnetic permeability which vary with temperature changes.

11 Claims, 4 Drawing Figures

PERMEABILITY RESPONSIVE OSCILLATOR FOR DETECTING PHASE TRANSFORMATIONS AT VARIOUS COOLING RATES

BACKGROUND OF THE INVENTION

This invention relates to a meter for producing, detecting and registering magnetic changes occurring in a material, such as steel, with temperature changes.

The great significance of steel as structural material is largely based on the possibilities of widely effecting its mechanical properties by means of heat treatments. In order to achieve a desired result a suitable steel, as to the decomposition properties of austenite, must be chosen at the same time considering available cooling possibilities.

The microstructure resulting from decomposition of austenite in steel, upon which microstructure the properties of steel depend, is normally presented as isothermal or continuous cooling phase transformation diagrams (IT- and CCT-diagrams) of which the latter has primarily practical significance.

Several methods are currently known for determination of such diagrams. Many of the methods used are only suitable for isothermal phase transformation studies. In principle, at least the following methods are known to be suitable for studies of continuous cooling: X-ray diffraction, resistance change measuring, dilatometer, magnetic measuring, thermic analysis.

On the basis of all these methods there have been efforts made to produce phase transformation meters but there have been such difficulties involved with measuring technique and equipment that only on the basis of the dilatometer method it has been possible to develop sets of equipment working at least satisfactorily. Thus, all phase transformation meters suitable for general use are dilatometers at the present time.

In the dilatometer method the detection of phase transformations is based on the detection of volumetric changes associated with these transformations. The test sample consists of a thin cylindrical rod whose alterations of length are transmitted by means of a quartz rod touching mechanically the end of the test rod to an inductive detector. Difficulties in this method are caused by the great measuring sensitivity required by small alterations of length and also a mechanical contact required between the measuring detector and the test rod. Therefore dilatometer equipment is not at all well suitable for phase transformation measurements occurring at high cooling rates ($> 100°$ C/s).

The magnetic changes associated with phase transformations have been attempted to be utilized when developing a phase transformation meter. This approach has been presented e.g. in Steel, January 1968, page 14. This device consists of two pairs of coils, one of them constituting a comparison pair. The coils are adjusted by means of bridge connections so that no current passes through the meter between the bridge connections. Now, when the magnetic properties of the test material change, they produce current between the coils, its magnitude being readable from the current meter and magnitude of the magnetic change occurred can be concluded therefrom. Like other similar equipment this set has not attained sufficient reliability, either. In addition, the use of two pairs of coils and quite a few bridge connections is cumbersome, as the current value obtained must nevertheless be transformed into estimated magnitude of phase transformation.

A device having commercial significance, in order to be superior as compared to equipment functioning according to the dilatometer principle, must comprise the following properties:

- the device must be suitable for phase transformation measurements also at high cooling rates ($\sim 100°$ C/s down to $1°$ C/min)
- measuring results are unambiguous and easily estimable
- the device is simply and easy operated
- the test sample is simple and inexpensive
- efficient life of the device is long
- it must be possible to simulate various practical cases and theoretical applications by means of the device.

OBJECTS AND SUMMARY OF THE INVENTION

The object of the invention is to provide equipment based on the detection of permeability changes and capable of meeting all above requirements.

The phase transformation meter according to the invention is characterized in that the sample to be examined is placed within a coil constituting inductance of a harmonic oscillator.

The invention is further characterized in that the equipment consists of several partial units, functions of them all being known as such, or directly derivable from physics. The partial units are as follows: observation unit for phase transformations, test sample and its fastening unit, heating and cooling unit for the test sample, temperature measuring unit, control and output unit.

BRIEF DESCRIPTION OF THE DRAWINGS

The invention will now be further described with reference to the accompanying drawings, in which.

DETAILED DESCRIPTION OF A PREFERRED EMBODIMENT

Figure 1:
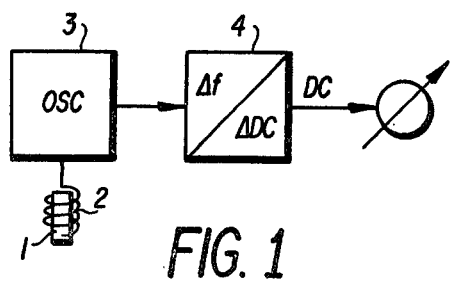
FIG. 1 represents the block diagram for the permeability meter of the present invention.
Figure 2:
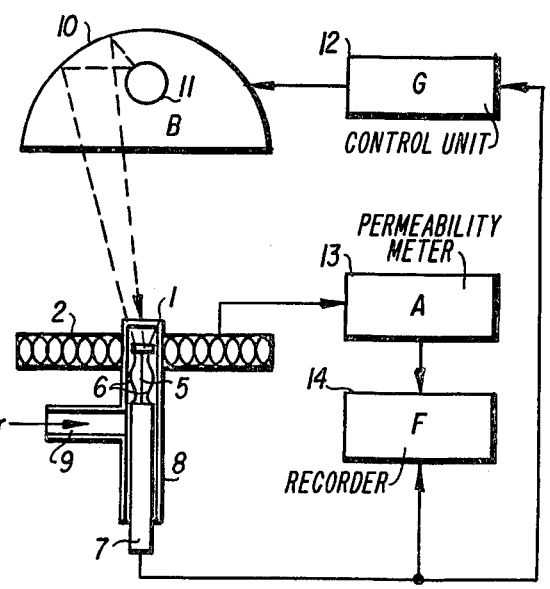
FIG. 2 shows the fastening assembly for the principle figure of the phase transformation meter in cross-section.

In the device of the invention the detection of phase transformations is based on measuring magnetic changes (i.e., permeability changes) in the test sample. It is known that austenite (and ferrite above Curie-temperature) is paramagnetic (relative permeability $\sim 1$) whereas ferrite is ferromagnetic below Curie-temperature. With decomposition of austenite below Curie-temperature, as the case usually is, the permeability of the test sample increases in proportion to the amount of ferrite produced. In the device of the invention the change in permeability of the test sample 1 is detected by means of a detection coil 2 surrounding the same. This detection coil is part of the harmonic oscillator 3 and it produces the impedance which sets the oscillation frequency of the oscillator.

The change in the permeability of the test sample effects the change in the impedance of the coil 2 which, in turn, effects the change in the frequency of the oscillator 3 which change is proportional to the magnitude of the permeability change. Additionally, a change in resistance takes place in the test sample resulting from the change in temperature and phase transformations. However, its effect on the change in frequency is of no significance as compared to permeability, although, with paramagnetic materials, it can be used as a source for corresponding observations. The change of frequency is altered, by using a per se known pulse technique, into directly proportional change of direct voltage in the transformation unit 4. The basic frequency used has been selected to be sufficiently great (2 600/s) in order to detect even very fast changes of permeability. Naturally it is possible to provide the meter with more than one basic frequency.

The test sample 1 used in the phase transformation meter of the invention is small and not dependent on any particular shape, although, from technical viewpoint, it is usually preferable to use a cylindrical test sample. The test sample 1 is fastened by welding with electric discharge to the sample holder 5. In the same way there are further fastened to the test sample 1 wires 6 of the Pt- PtRh-thermocouple. The sample holder 5 is in turn secured to the stand 7 of the sample holder. The test sample 1, the thermocouple 6, the sample holder 5 and partly its stand 7 are placed within a quartz glass tube 8 positioned with regard to the coil 2 so that the test sample 1 lies as centrally as possible within the coil 2. Argon as a protective gas is fed to the quartz glass tube 8 from a separate source, not shown, through a tap 9. The purpose of the gas is to prevent oxidation of and to cool the sample. Radiation heat is used for heating the test sample, since it does not disturb the measuring of the permeability and the temperature. The test sample is placed in one focus of an elliptical mirror (10) and an effective halogen or heat lamp 11 in the other.

The effect of the lamp is regulated by means of a stepless programming control unit 12, which can be programmed with various cooling curves. A feed back connection couples the control unit to the thermocouple 6. Both the permeability meter 13 and the thermocouple are connected to different channels of the recorder 14.

Figure 3:
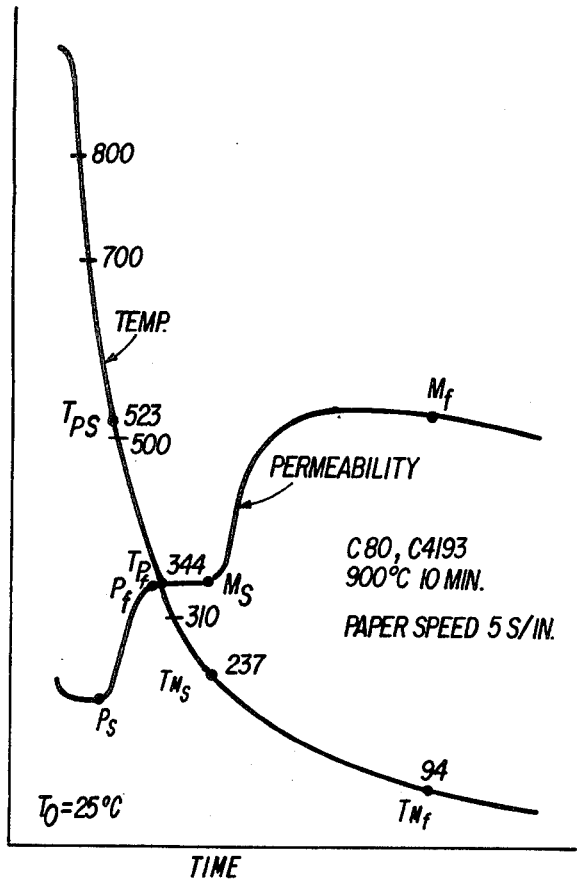
FIG. 3 shows a typical measuring output.
Figure 4:
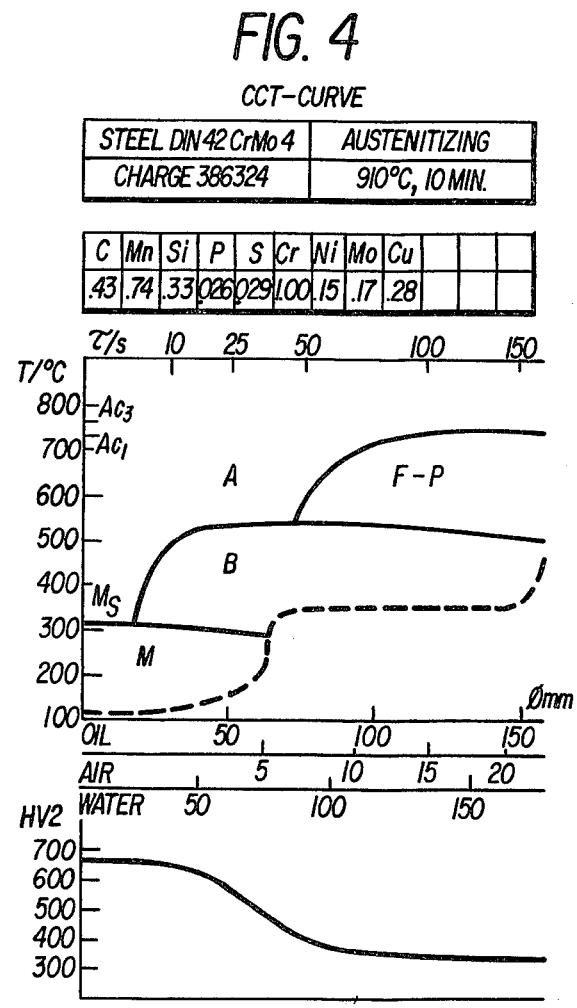
FIG. 4 is a phase transformation diagram (CCT-diagram) prepared on the basis of the output.

FIGS. 3 and 4 illustrate the output of the phase transformation meter of the present invention and the resulting CCT diagram, respectively.

The graphs in FIG. 3 indicate the change in temperature as a function of time, i.e., cooling curve, and the change in sample permeability as a function of temperature.

The designations used in FIG. 3 are as follows:

| | |
|---|---|
| $T_o = 25°$ C | represents room temperature, i.e., the temperature to which the sample cools. |
| $P_s$ | is located at the lowest point of the permeability curve in Figure 3, and represents the start of perlite formation. |
| $T_{P_s}$ | represents the temperature corresponding to $P_s$, i.e., the temperature at which perlite formation begins. |
| $P_f$ | represents the conclusion of perlite formation. |
| $T_{P_f}$ | represents the temperature corresponding to $P_f$ i.e., the temperature at which perlite formation is finished. |
| $M_s$ | represents the start of martensite formation. |
| $T_{Ms}$ | represents the temperature corresponding to $M_s$, i.e., the temperature at which martensite formation begins. |
| $M_f$ | represents the conclusion of martensite formation. |
| $T_{Mf}$ | represents the temperature corresponding to $M_f$ i.e., the temperature martensite formation is finished. |
| C 80 | represents the type of carbon steel used in this example (corresponds to AISI 1080 or SAE 1080). |
| C4193 | represents the melting code (Charge 4193) employed. |
| 900° C 10 min | represents the austenitizing temperature and time used in the test. |
| paper speed | 5 s/in represents the recording paper speed used in measuring. |
| $\tau = 5{,}6$ | represents the time constant for the temperature curve illustrating the steepness of the curve i.e., cooling rate. |

FIG. 4 represents a CCT diagram of a steel sample prepared from measurements made with the phase transformation of the present invention. As will be readily apparent to one skilled in the art such a diagram can be prepared by utilizing data relating to phase transformation at various cooling rates, e.g., cooling in oil, air, water.

The designations used in FIG. 4 are as follows:

| | |
|---|---|
| Charge 386324 | is an identification number for the particular steel composition (shown thereafter) employed in developing the curves shown in Figure 4. |
| Austenitizing | refers to heat treatment of the steel at 910° C for ten minutes thereby converting the steel into austinite. |
| A | refers to austenite. |
| F–P | refers to ferrite-perlite. |
| B | refers to banite. |
| M | refers to martensite. |
| $M_s$ | refers to the formation of martensite upon cooling. |
| $Ac_3$ | refers to the temperature above which the steel is totally austenite. |
| $Ac_1$ | refers to the temperature below which the steel is totally ferrite. |
| $\tau/s$ | refers to the cooling rate (in seconds) from 700° C to 500° C. refers to the particular cooling medium employed. For example, "OIL 50" means that a steel rod with a 50 mm diameter will cool in the center from 700° C to |

| | -continued |
|---|---|
| Air<br>OIL<br>WATER | 500° C in 25 seconds. This information is seen by referring to the lower right hand portion of the curve where the φ mm refers to the rod diameter in combination with the cooling rate ( 96 /s). Thus, φ 50 is seen on the oil scale which corresponds to 24 seconds on the τ/s scale. |
| HV2 | refers to the Vickers hardness (H) in the center of the rod formed in the rod treated in the manner shown in the upper graph. The hardness is measured with a 2kg weight. Values of 300–700 refer to kg/sq. mm. |

Examination of phase transformations of the test sample 1 is carried out as follows with the set of equipment:

The desired cooling curve has been programmed on the control unit 12. The test sample with its sample holder 5 and stand 7 is placed in position and the protective gas is fed through the tap 9 into the quartz tube 8. The lamp 11 is turned on. After the sample has reached sufficient temperature, the permeability meter 13, the recorder 14 and the control means 12 are turned on. Now the control unit 12 adjusts the effect of the lamp 11 so that the cooling follows the desired curve. Thus, the curves of FIG. 3 is produced, showing temperature and changes of test sample permeability and, according to these, it is easy to define initial and terminal points of different phase transformations.

By executing a sufficient number of tests at various cooling rates it is, on the basis of these tests, possible to plot very reliably and, compared to dilatometer measures, also very fast a CCT-diagram characteristic for each steel.

The method of the invention is also the major advantage that test samples are very easy to manufacture and position in the device. Furthermore, since the test sample is small and there is no heat transfer from the environment, it is possible to reliably simulate very fast coolings. In addition, the set of equipment can be used for simulation of considerably more complicated arbitrary heat treatments.

What we claim is:

1. A device for detecting phase transformations in a magnetic permeable material as a function of temperature change comprising:
   test sample holding means;
   heating means for automatically effecting a variety of elevated temperatures in the sample being tested;
   means for automatically and rapidly controlling the cooling rate of said test sample after it has been heated to said elevated temperature;
   means for detecting phase transformations of said sample being tested as a function of temperature by changes in the magnetic property of said test sample as said sample cools from its elevated temperature, said detecting means including a coil operatively coupled to said test sample, a harmonic oscillator operatively coupled to said coil, said coil constituting the frequency determining inductance of said oscillator;
   means for automatically sensing the temperature of said sample as it cools;
   whereby phase changes in the test sample cause changes of the magnetic properties of said magnetic permeable material which in turn cause changes in the oscillator frequency of said harmonic oscillator, said frequency being detected along with the temperature to yield information for use in preparing continuous cooling phase transformation diagrams.

2. The device according to claim 1 wherein said cooling means yield cooling rates of said sample being tested of at least about 100° C/sec.

3. The device according to claim 2 wherein said cooling means is an inert fluid.

4. The device according to claim 1 wherein said heating means comprise a radiation source and eliptical-type reflector means for directing said radiation to said test sample.

5. The device according to claim 4 wherein said sample is positioned in one focus of said reflector means and said radiation source is positioned in another focus of said reflector means.

6. The device according to claim 1 wherein said test sample holding means includes a radiation transparent protective tube having one end closed, said heating being effective through said closed end, said test sample being positionable through said open end.

7. The device according to claim 6 including means for passing cooling fluid into said protective tube.

8. The device according to claim 1 wherein said oscillator frequency changes are converted to direct voltage.

9. The device of claim 8, wherein the change of direct voltage is directly proportional to the oscillator frequency change.

10. The device of claim 1, wherein the frequency change is converted into digital form.

11. The device of claim 1, wherein the frequency of the harmonic oscillator is 2000 (cycles/sec).

* * * * *